US010675213B2

United States Patent
Wijshoff et al.

(10) Patent No.: US 10,675,213 B2
(45) Date of Patent: Jun. 9, 2020

(54) DETERMINING RETURN OF SPONTANEOUS CIRCULATION DURING CPR

(71) Applicant: KONINKLIJKE PHILIPS N.V., Eindhoven (NL)

(72) Inventors: Ralph Wilhelm Christianus Gemma Rosa Wijshoff, Munstergeleen (NL); Jens Muehlsteff, Aachen (DE); Simone Cornelia Maria Anna Ordelman, s'Hertogenbosch (NL); Wouter Herman Peeters, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 222 days.

(21) Appl. No.: 15/738,842

(22) PCT Filed: Jun. 23, 2016

(86) PCT No.: PCT/EP2016/064593
§ 371 (c)(1),
(2) Date: Dec. 21, 2017

(87) PCT Pub. No.: WO2016/207306
PCT Pub. Date: Dec. 29, 2016

(65) Prior Publication Data
US 2018/0177678 A1    Jun. 28, 2018

(30) Foreign Application Priority Data
Jun. 26, 2015    (EP) .................................... 15173963

(51) Int. Cl.
*A61H 31/00*    (2006.01)
*A61B 5/0205*   (2006.01)
(Continued)

(52) U.S. Cl.
CPC ......... *A61H 31/005* (2013.01); *A61B 5/0205* (2013.01); *A61B 5/0245* (2013.01);
(Continued)

(58) Field of Classification Search
None
See application file for complete search history.

(56) References Cited

U.S. PATENT DOCUMENTS

2004/0215244 A1    10/2004   Marcovecchio et al.
2008/0013747 A1    1/2008    Tran
(Continued)

FOREIGN PATENT DOCUMENTS

EP         2883493 A2       6/2015
WO      2012114286 A1       8/2012
(Continued)

OTHER PUBLICATIONS

Eberle et al: "Checking the Carotid Pulse Check: Diagnostic Accuracy of First Responders in Patients With and Without a Pulse"; resuscitation 33 (1996) 107-116.
(Continued)

*Primary Examiner* — Ankit D Tejani

(57) ABSTRACT

A device for supporting determination of return of spontaneous circulation, ROSC, during an associated cardiopulmonary resuscitation, CPR, procedure which is being performed on an associated patient. A sensor is used to sense a physiological signal of the patient. Frequency analysis of the signal is carried out to extract dominant fundamental frequency components in the signal. From this analysis it is possible to determine that there has been a potential ROSC.

15 Claims, 7 Drawing Sheets

(51) Int. Cl.
| | |
|---|---|
| A61B 5/026 | (2006.01) |
| A61B 5/00 | (2006.01) |
| A61B 5/024 | (2006.01) |
| A61B 5/0245 | (2006.01) |
| A61B 5/044 | (2006.01) |
| A61B 5/083 | (2006.01) |
| A61B 5/11 | (2006.01) |
| A61N 1/39 | (2006.01) |
| A61B 5/0456 | (2006.01) |
| A61B 5/1455 | (2006.01) |
| A61B 5/08 | (2006.01) |

(52) U.S. Cl.
CPC ........ *A61B 5/0261* (2013.01); *A61B 5/02416* (2013.01); *A61B 5/044* (2013.01); *A61B 5/0456* (2013.01); *A61B 5/0836* (2013.01); *A61B 5/11* (2013.01); *A61B 5/14551* (2013.01); *A61B 5/4848* (2013.01); *A61B 5/7253* (2013.01); *A61B 5/7275* (2013.01); *A61B 5/7282* (2013.01); *A61B 5/742* (2013.01); *A61N 1/3925* (2013.01); *A61B 5/082* (2013.01); *A61B 5/0809* (2013.01); *A61B 5/7203* (2013.01); *A61B 5/746* (2013.01); *A61B 5/7435* (2013.01); *A61B 2505/01* (2013.01); *A61N 1/3937* (2013.01)

(56) References Cited

U.S. PATENT DOCUMENTS

| | | | |
|---|---|---|---|
| 2011/0004069 A1 | 1/2011 | Ochs et al. | |
| 2012/0010543 A1 | 1/2012 | Johnson et al. | |
| 2013/0296727 A1 | 11/2013 | Sullivan et al. | |
| 2013/0304142 A1 | 11/2013 | Curtin et al. | |
| 2013/0338724 A1 | 12/2013 | Joo et al. | |
| 2014/0107541 A1 | 4/2014 | Sullivan et al. | |
| 2014/0213941 A1 | 7/2014 | Johnson et al. | |
| 2014/0236053 A1 | 8/2014 | Walker et al. | |
| 2014/0336546 A1 | 11/2014 | Chapman et al. | |
| 2015/0112401 A1* | 4/2015 | Sullivan | A61B 5/7217 607/5 |
| 2015/0164339 A1* | 6/2015 | Xu | A61B 5/024 600/324 |

FOREIGN PATENT DOCUMENTS

| | | |
|---|---|---|
| WO | 2013181376 A1 | 12/2013 |
| WO | 2015121114 A1 | 8/2015 |

OTHER PUBLICATIONS

Falk et al:"End-Tidal Carbon Dioxide Concentration During Cardiopulmonary Resuscitation"; N. Eng. J. Med. vol. 318, No. 10, pp. 607-611, 1988.

Herardstveit et al: "Factors Complicating Interpretation of Capnography During Advanced Life Suppport in Cardiac Arrest—A Clinical Retrospective Study in 575 Patients"; Resuscitation, 83, 2012, 813-818.

Neumar et al: "Part 8: Adult Advanced Cardiovascular Life Support:2010 American Heart Association Guidelines for Cardiopulmonary Resuscitation and Emergency Cardiovascular Care"; Circulation 2010, 122, No. 18, Suppl 3, pp. S729-S767.

Nolan:"High Quality Cardiopulmonary Resuscitation"; Curr. Opin. Crit. Care, vol. 20, pp. 1-7, 2014.

Steedman et al: "Measurement of End-Tidal Carbon Dioxide Concentration During Cardiopulmonary Resuscitation"; Archives of Emergency Medicine, 1990, 7, 129-134.

Tibbals et al: "Reliability of Pulse Palpitation by Healthcare Personnel to Diagnose Paediatric Cardiac Arrest"; Resuscitation, 80, 2009, 61-64.

Wijshoff et al: "Detection of a Spontaneous Pulse in Photoplethysmograms During Atuomated Cardiopulmonary Resuscfitation in a Porcine Model"; Resuscitation 84, 2013, 1625-1632.

Wijshoff et al: "Abstract 137: A Photoplethysmography Signal Can Show the Presence of a Spontaneous Pulse at Sub-Life-Supporting Blood Pressure During Experimental Cardiopulmonary Resuscitation"; Circulation, vol. 130, No. Supp2, p. A137, 2014.

Wik et al: Quality of Cardiopulmonary Resuscitation During Out-Of-Hospital Cardiac Arrest; JAMA, 2005, 293 (3), pp. 299-304.

Ordelman et al: "Low Minute Ventilation Volume During CPR Disturbs the Relationship Between End-Tidal CO2 and Coronary Perfusion Pressure"; Circulation, 2013, 128:A290.

Wijshoff et al: "Photoplethysmography-Based Algorithm for Detection of Cardiogenic Output During Cardiopulmonary Resuscitation"; IEEE Transactions on Biomedical Engineering, vol. 62, No. 3, Mar. 2015, pp. 909-921.

Wijshoff et al:"Photoplethysmography to Guide Pulse Checks During Cardiopulmonary Resuscitation:Observations in an Animal Study"; Resuscitation 2013, vol. 84, p. S1, Oct. 2013.

* cited by examiner

DETERMINING RETURN OF SPONTANEOUS CIRCULATION DURING CPR

CROSS-REFERENCE TO PRIOR APPLICATIONS

This application is the U.S. National Phase application under 35 U.S.C. § 371 of International Application No. PCT/EP2016/064593, filed on Jun. 23, 2016, which claims the benefit of European Patent Application No. 15173963.8, filed on Jun. 26, 2015. These applications are hereby incorporated by reference herein.

FIELD OF THE INVENTION

The present invention relates to the field of determining return of spontaneous circulation, in particular the invention relates to a device, method and computer program for supporting the determination of return of spontaneous circulation during cardiopulmonary resuscitation.

BACKGROUND OF THE INVENTION

Cardiopulmonary resuscitation for cardiac-arrest patients is an emergency procedure with a very low survival rate (5-10%). It is commonly accepted that the quality of the chest compressions is of crucial importance for successful defibrillation and outcome.

Detecting return of spontaneous circulation (ROSC) during cardiopulmonary resuscitation (CPR) is challenging. Typically, ROSC detection involves manual palpation for an arterial pulse, for example at the neck of the patient. Manual palpation requires interrupting the chest compressions and is known to be time-consuming, which can therefore lead to reduced blood flow and a reduced chance of ROSC.

To minimize the duration of this type of pause, clinical guidelines state that a pulse-check pause should take no longer than 10 seconds. In clinical practice, manual pulse checks often take much longer than 10 seconds and are known to be unreliable even if performed by expert clinicians.

Alternatively, a reliable and objective measurement to support ROSC detection is an arterial blood pressure measurement, which can be interpreted to indicate ROSC when the systolic blood pressure is higher than, e.g., 60 mmHg. However, this is an invasive measurement which requires placement of catheters and is consequently not always available. Therefore, a non-invasive method that can support ROSC detection during ongoing chest compressions would be a valuable asset.

The reference US 2012/0035485A1 describes that the presence of a cardiac pulse in a patient may be determined by evaluating physiological signals in the patient. In one embodiment, a medical device evaluates optical characteristics of light transmitted into a patient to ascertain physiological signals, such as pulsatile changes in general blood volume proximate a light detector module. Using these features, the medical device determines whether a cardiac pulse is present in the patient. The medical device may also be configured to report whether the patient is in a VF, VT, asystole, or PEA condition, in addition to being in a pulseless condition, and prompt different therapies, such as chest compressions, rescue breathing, defibrillation, and PEA-specific electrotherapy, depending on the analysis of the physiological signals. Auto-capture of a cardiac pulse using pacing stimuli is further provided.

Reference R.W.C.G.R. et Al: "Detection of a spontaneous pulse in photoplethysmograms during automated cardiopulmonary resuscitation in a porcine model", RESUSCITATION, vol. 84, 2013, pages 1625-32, XP55125349 discloses an investigation of the potential of photoplethysmography (PPG) signals to detect the presence and rate of a spontaneous cardiac pulse during CPR, by retrospectively analyzing PPG and arterial blood pressure signals simultaneously recorded in pigs undergoing automated CPR.

EP 2 883 493 discloses a system for real-time recognition of restoration of spontaneous circulation which uses time-domain and frequency-domain recognition logic. US 2013/0338724 discloses a system which uses two or more physiological signals to detect a cardiac pulse.

Thus, there have been various attempts to monitor physiological signals to detect the presence of a spontaneous pulse. Monitoring of end-tidal CO2, invasive blood pressure, or central venous oxygen saturation, allows for an objective assessment of pulse, but requires a secured airway or placement of catheters. Trans-thoracic impedance (TTI) measurements, and near-infrared spectroscopy (NIRS) are non-invasive, but TTI is strongly influenced by chest compressions and NIRS responds slowly upon ROSC.

While analysis of photoplethysmography data for pulse detection has been proposed, the data is not easy to interpret.

There remains a need for a reliable way to detect ROSC in a non-invasive way and without interrupting the chest compression sequence being performed on an associated patient. In particular, there is a need for a fast, automated, and accurate method to do a pulse check which gives simple to interpret results, so as to reduce the duration of any pauses and to reduce the amount of false pulse determinations. Recording of the electrocardiogram (ECG) alone does not provide the information as the heart may be electrically active but may not produce cardiac output.

SUMMARY OF THE INVENTION

Examples in accordance with a first aspect of the invention provide a device for supporting determination of return of spontaneous circulation, ROSC, during an associated cardiopulmonary resuscitation, CPR, procedure which is being performed on an associated patient, the device comprising:
an input for receiving a signal from a sensor for sensing a physiological signal of the patient;
a processor, which is adapted to:
perform frequency analysis of the physiological signal;
detect and discriminate compression-induced components and spontaneous pulse components within the physiological signal;
provide an output based on the detected components within the physiological signal to support determination that there has been ROSC; and
a display device,
wherein the processor is adapted to control the display device to output an image which shows the compression-induced components and spontaneous pulse components within the physiological signal, over time as a frequency-time plot.

This invention is based on a frequency analysis of a physiological signal, such as a photoplethysmography (PPG) signal and/or an electrocardiography (ECG) signal acquired during CPR. By analyzing a physiological signal to extract the compression-induced components and the spontaneous pulse components, information about the CPR as well as any spontaneous pulse may be provided to a clinician, to assist them in determining that there has been ROSC.

The image output may for example involve displaying the dominant frequency components in the sensor signal. These dominant frequency components may be shown as they evolve over time.

Such a time-frequency representation can simultaneously provide visual feedback on the rate at which the chest compressions are delivered (which can be used to assess CPR quality), and the absence or presence of an underlying spontaneous pulse based on the physiological signal (PPG and/or ECG). Feedback on the absence or presence of an underlying spontaneous pulse, and the CPR feedback, may then be provided during ongoing chest compressions.

The displayed information may comprise a first trace which visually provides feedback about the rate at which the chest compressions are delivered over time throughout the CPR event. Feedback on chest compression rate can support the caregiver to deliver chest compressions at a rate of 100-120 per minute as advised in CPR guidelines.

If a heart rate is detected in an ECG signal or an underlying spontaneous pulse is detected in a PPG signal during CPR, this can be shown in the time-frequency representation by using an additional trace different from the trace indicating the chest compression rate over time. Specifically, the time-frequency representation may then show the history of the chest compression rate delivered throughout the CPR event as well, which serves as a reference to facilitate recognizing the appearance of the traces indicating the heart rate and the spontaneous pulse rate.

Simultaneously showing the heart rate (i.e. electrical heart activity) and the pulse rate (a perfusing heart rhythm) in a single time-frequency representation furthermore facilitates determining whether each R peak in the ECG leads to a contraction of the heart.

In one example, the processor is adapted to extract dominant fundamental frequency components of harmonic frequency series within the physiological signal and provide an output based on the extracted dominant fundamental frequency components to support determination that there has been ROSC.

By extracting the dominant fundamental frequency components, easy to interpret information may be provided to the clinician. The analysis may also enable determination of a potential ROSC automatically. The automatic determination of a potential ROSC may however be based on the analysis of the full harmonic series. This automatic determination of a potential ROSC may be used by a clinician as further guidance, rather than providing an absolute indication of ROSC. Note that determining whether a patient has ROSC is a clinical, situational assessment. It not only involves determining whether there is a spontaneous pulse, but it also involves determining whether the output (blood flow) generated by the heart is life-sustaining. This is an assessment which only can be made by a medical doctor, as the cardiac output needed to stay alive varies from one patient to the other and even varies over time within one patient. The monitoring equipment supports the clinician in determining whether there is ROSC by showing information derived from measurements.

The output signal provides information automatically about ROSC and can be used to avoid the need to take pulse checks during CPR if there is no spontaneous pulse. The output can guide the clinician as to when pulse checks should be taken, or when administration of vasopressors is appropriate. A frequency analysis representation of the PPG signal can objectively show whether an underlying spontaneous pulse is present during CPR. Unnecessary interruptions in chest compressions for lengthy and futile pulse checks can be prevented in case of pulse absence, which can improve CPR outcome. Vasopressors may have detrimental effects on cardiovascular stability if administered just after the heart has started beating again. The system can thus be used to prevent administration of vasopressors when these may have detrimental effects, by advising a clinician during ongoing compressions whether a spontaneous pulse is present.

The processor is for example adapted to perform frequency analysis of at least the fundamental frequency components and the first harmonic components present in the physiological signal.

By analyzing multiple frequency components, it is possible to distinguish more reliably between a pulse induced by the CPR and a spontaneous pulse. In particular, differences may be greater between the higher harmonic frequency components than the fundamental frequency components. Frequency analysis may be carried out of at least the second harmonic components present in the physiological signal.

The sensor for example may comprise an ECG sensor and/or a PPG sensor.

A second sensor or sensors may also be provided for sensing the CPR compressions and/or a capnography signal (which measures concentration or partial pressure of CO2). A CPR sensor can be used to give a clinician feedback about the quality of CPR being delivered, such as the compression depth and the compression rate. A capnography signal sensor may be used to assist in more reliable interpretation of the physiological sensor e.g. PPG signal. This provides a means to better assess the adequacy/quality of a spontaneous pulse component in a PPG signal.

The processor is thus preferably adapted to determine the quality of any determined ROSC. This may be based on a signal to noise analysis of the spontaneous pulse signal, or an energy measurement of the spontaneous pulse signal. Thus, the processor may be adapted to control the display device to output an image which shows:
  the quality of the CPR compressions; and/or
  the quality of any determined ROSC.

Examples in accordance with another aspect of the invention provide a method for supporting determination of return of spontaneous circulation, ROSC, during an associated cardiopulmonary resuscitation, CPR, procedure which is being performed on an associated patient, the method comprising:
  sensing a physiological signal of the patient;
  performing frequency analysis the physiological signal;
  detecting and discriminating compression-induced components and spontaneous pulse components within the physiological signal; and
  providing an output on a display device based on the detected components within the physiological signal to support determination that there has been ROSC, wherein the output shows the compression-induced components and spontaneous pulse components within the physiological signal over time as a frequency-time plot.

This method provides support to a clinician to support determination of ROSC. It may provide automatic recognition of a potential ROSC during CPR.

The determined recognition of a potential ROSC is for example displayed to a user.

The frequency analysis may involve extracting dominant fundamental frequency components of harmonic frequency series within the physiological signal. The extracted dominant fundamental frequency components are preferably also displayed in the form of a frequency versus time plot.

As explained above, the frequency analysis may be performed on at least the fundamental frequency components and the first harmonic components present in the physiological signal, and optionally also at least the second harmonic components present in the physiological signal.

The method may further comprise sensing the CPR compressions and determining the quality of the CPR compressions.

The method preferably also comprises outputting an image on a display device, which image shows:
the quality of the CPR compressions; and/or
the quality of any determined potential ROSC.

This information is preferably shown over time so that the evolution of the signals can be seen.

The invention also provides a computer program (and a computer program carrier) for implementing the method defined above.

BRIEF DESCRIPTION OF THE DRAWINGS

Embodiments of the invention will be described, by way of example only, with reference to the drawings, in which.

DETAILED DESCRIPTION OF THE EMBODIMENTS

The invention provides a device for supporting determination of return of spontaneous circulation, ROSC, during an associated cardiopulmonary resuscitation, CPR, procedure which is being performed on an associated patient. A sensor is used to sense a physiological signal of the patient. Frequency analysis of the signal is carried out, for example to detect dominant frequency components in the signal. From this analysis it is possible to support determination that there has been ROSC by preparing an output for a clinician which enables easy and rapid further interpretation.

Figure 1:
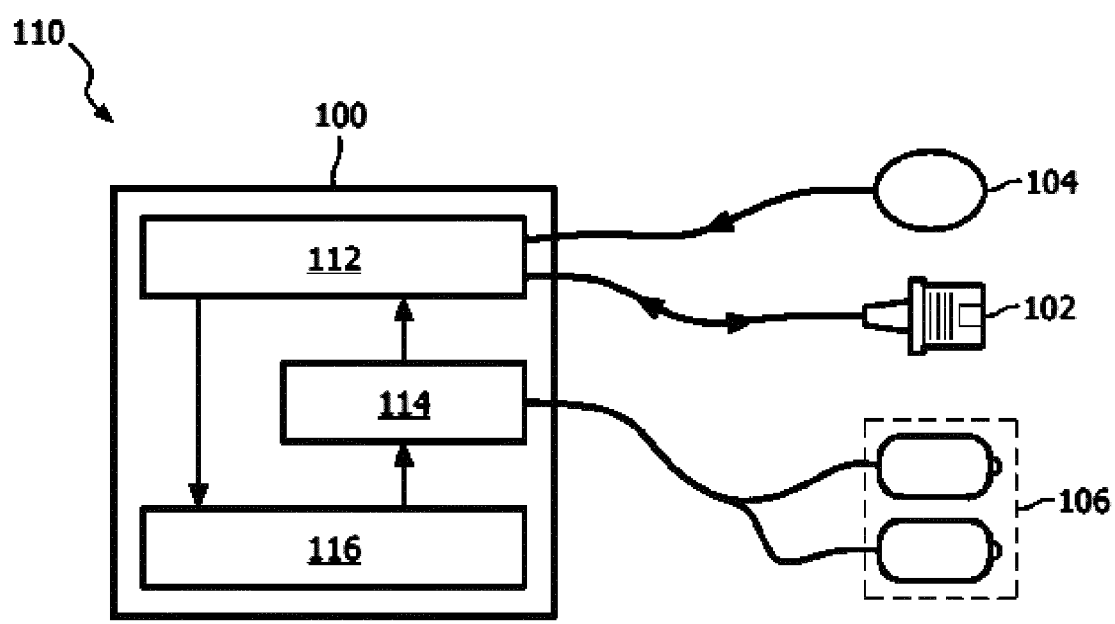
FIG. 1 shows a first example of a patient monitoring system in accordance with the invention.

FIG. 1 shows a system 110 comprising a device 100 for supporting determination of return of spontaneous circulation, ROSC, during an associated cardiopulmonary resuscitation, CPR, procedure. The device 100 functions as a patient monitor. In this example, it also functions as a defibrillation device in the sense that it comprises electronics 114 for controlling defibrillator pads 106.

The device receives an input from a physiological sensor 102, which may be a commercial PPG sensor or an ECG monitor. The device 100 contains a controller 112 with access to or comprising one or more predetermined algorithms.

The system also comprises a display 116.

The device is connected to a defibrillator, such as a set of defibrillator pads 106. This allows the algorithm to know when the shock is given and to obtain information on the chest compressions via, e.g., a transthoracic impedance measurement.

The device may be used for monitoring a patient during manual CPR, but it may also be used with an automated CPR device.

A second input to the device 100 receives a sensor signal from a CPR monitor such 104 such as an accelerometer. This provides information concerning CPR compression frequency, phase, and acceleration, velocity and depth as well as compression pauses.

In alternative embodiments, the system does not comprise the defibrillator pads 106 and/or the automated CPR device and/or the accelerometer 104.

The controller performs frequency analysis of the sensed physiological signal. In one set of examples, it extracts dominant fundamental frequency components of the physiological signal. An output is provided to the display based on the frequency analysis, for example based on the extracted dominant fundamental frequency components, to support the clinician to determine that there has been ROSC.

Figure 2:
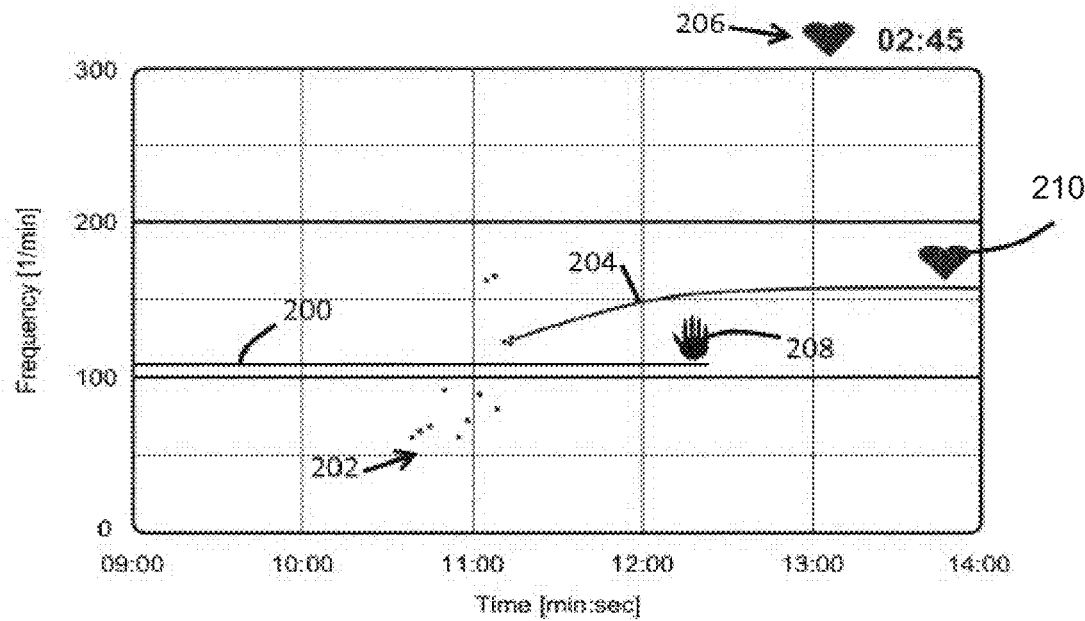
FIG. 2 shows a first example of possible display output.

FIG. 2 shows a first example of possible display output.

The output is in the form of a time-frequency representation showing the fundamental compression rate (line 200), arrhythmic spontaneous pulses (dots 202) and the stable fundamental spontaneous pulse rate (line 204). The pulses 202 occur when the heart restarts beating again.

The lines may have a width which represents how variable the frequency is, so the wider the line, the more variable the frequency is. This is not shown.

A timer 206 indicates the duration of the period that a stable spontaneous pulse has been detected uninterruptedly.

The time-frequency representation in FIG. 2 shows a 5 minute episode of CPR. The x-axis shows time in minutes:seconds, starting at 9 minutes (after an arbitrary starting point) and ending at 14 minutes. The y-axis shows the frequency.

CPR compressions are delivered from 09:00 up to about 12:25. A stable spontaneous pulse appears at about 11:15. Between 10:30 and 11:15 arrhythmic spontaneous pulses have been detected in the PPG signal, as indicated by the dots 202. As spontaneous pulses occur at irregular intervals, no pulse rate exists.

Symbols indicating the chest compression rate (hand 208) and spontaneous pulse rate (heart 210) are positioned at the most recent point of the trace.

The history of the delivered compression rates facilitates detecting the change in the representation occurring at 11:15. The timer 206 starts running from the moment that a stable spontaneous pulse rate has been detected in the PPG signal, indicating the duration that a spontaneous pulse has been detected.

Figure 3:
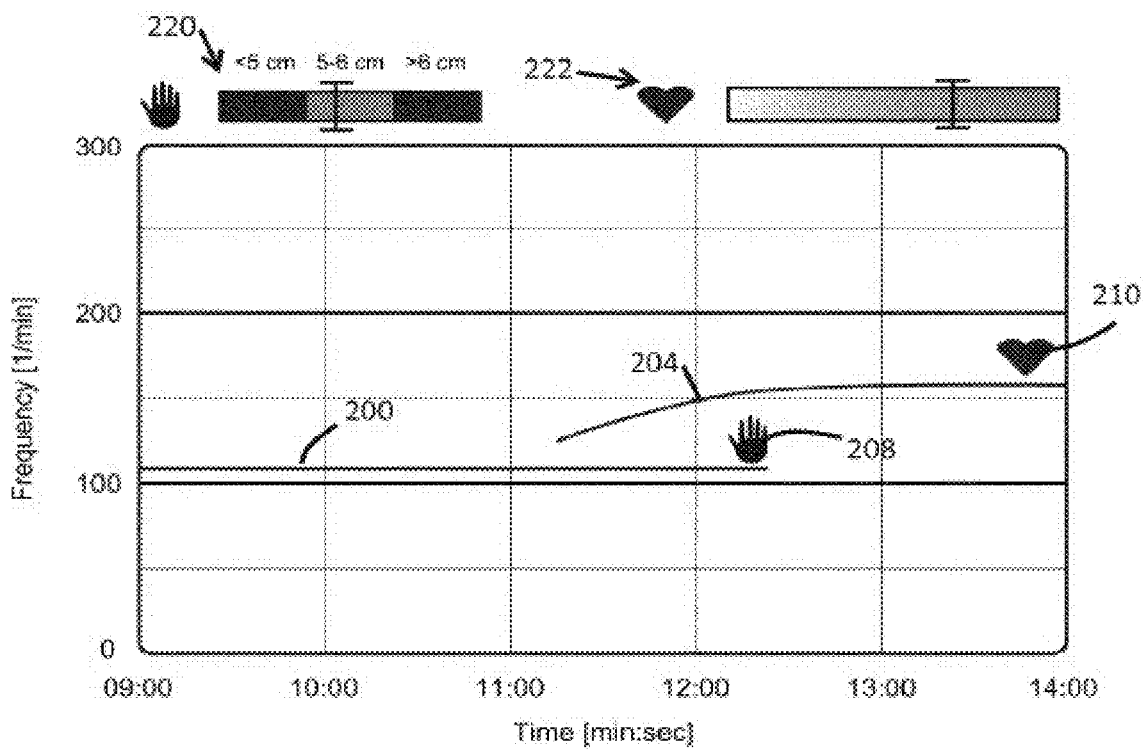
FIG. 3 shows a second example of possible display output.

In FIG. 3 a spontaneous pulse has been detected for 02:45 minutes. Should the spontaneous pulse disappear again, then the timer will freeze. If a stable spontaneous pulse subsequently re-appears, the timer will start running again from 00:00.

Showing the duration that a stable spontaneous pulse has been detected uninterruptedly supports the clinician in deciding when to interrupt the chest compressions to determine whether the spontaneous pulse is palpable and there is ROSC.

To arrive at this time-frequency representation, the physiological signal (e.g. PPG signal) is processed and analyzed in the time and frequency domains as explained above. Time domain analysis is employed to detect the arrhythmic pulses, indicated by the dots 202. Frequency domain analysis will provide an averaged pulse rate. Via time-domain analysis arrhythmic beats can be detected individually, which is used to, e.g., determine the position of the individual dots 202 in FIG. 2.

Frequency analysis is employed to identify the harmonic series corresponding to the chest compressions and the harmonic series corresponding to the spontaneous pulse rate. The frequency analysis can be performed by Fourier analysis, autoregressive modeling or wavelets. In this way, both compression-induced components and spontaneous pulse components are detected and discriminated within the physiological signal. A single physiological signal is analyzed to extract these components. In the preferred example, the single signal is a PPG signal. As explained above, the system may however have multiple physiological sensors, and in this way the information provided to the clinician can be further refined.

At 11:15 the algorithm has detected presence of a sufficiently strong spontaneous pulse component in the PPG signal, based for example on the signal-to-noise ratio, the number of harmonics, or the accumulated energy in all the harmonics. However, only the fundamental frequencies of these series are shown in the time-frequency representation for clarity, and higher harmonics are omitted. Also background noise present in the signals is not shown.

The chest compression rate may be identified either by analyzing the harmonic series present in the physiological signal, or by analyzing the independent measurement of compressions using sensor 104. The harmonic series in the physiological signal corresponding to the compressions can be identified by determining the number of harmonics present in the signal or the total power in the series relative to the noise floor. As compressions result in steeper pulses than a cardiac contraction, the harmonic series corresponding to the compressions contains more components than the harmonic series corresponding to the spontaneous pulse.

The independent measurement of compressions may be based on a sensor 104 in the form of an accelerometer integrated with the physiological sensor, a QCPR-pad, a radar sensor, a pressure/force sensor or a trans-thoracic impedance measurement. Any other means to obtain information on the compression rate and/or acceleration and/or speed and/or depth and/or force and/or pressure may be used.

The heart rate may additionally be measured by an ECG sensor, and the pulse rate may then be shown in the same time-frequency representation. This facilitates determining whether each R peak in an ECG signal leads to a contraction of the heart. Specifically detection of pulseless electrical activity (PEA) can be readily done, when an ECG-based heart rate (i.e. electrical heart activity but not a perfusing pulse) is present in the time-frequency representation, but simultaneously no spontaneous pulse rate (i.e. a perfusing pulse) can be detected in the PPG signal.

In FIG. 2, the fundamental frequency components of the chest compression rate and the spontaneous pulse rate are shown in one time-frequency representation. In another embodiment, two time-frequency representations can be shown, one providing feedback on the rate at which the chest compressions are being delivered, and one providing feedback on presence or absence of an underlying spontaneous pulse.

The time-frequency representation can be shown on the monitoring device 100, for example the display of a monitor-defibrillator, or the display of an automated external defibrillator (AED).

Additionally, the monitoring device 100 may wirelessly communicate the time-frequency representation to a separate device that serves as a display only, for example a smartphone or a tablet, which can be positioned next to the victim so it is easily observed by the caregiver while delivering chest compressions and ventilations. A headset device (such as Google glass) may also be used to display information to the user, while enabling them to continue concentrating on the task they are performing.

The required physiological sensor can be a PPG sensor, either transmissive or reflective, or a non-contact sensing means such as a camera. This sensor can also be an ECG measurement using one or more leads. These may form part of the defibrillator pads.

One suitable system for obtaining PPG (pulse oximetry) data includes a sensor with a red LED, a near-infrared LED, and a photodetector diode, where the sensor is configured to place the LEDs and photodetector diode directly on the skin of the patient, typically on a digit (finger or toe) or earlobe. Other places on the patient may also be suitable, including the forehead, the nose or other parts of the face, the wrist, the chest, the nasal septum, the alar wings, the ear canal, and/or the inside of the mouth, such as the cheek or the tongue. The LEDs emit light at different wavelengths, which light is diffused through the vascular bed of the patient's skin and received by the photodetector diode. The resulting PPG signal may then be analyzed for one or more features indicative of a cardiac pulse. Other simpler versions of a system for obtaining PPG data may be used, including a version with a single light source of one, e.g., green, or more wavelengths. The absorption or reflectance of the light is modulated by the pulsatile arterial blood volume and detected using a photodetector device. In an embodiment, PPG data can be obtained from camera images, where ambient light and/or additional light sources are used to illuminate the tissue, such as skin.

PPG measurements can be carried out at a distance from the tissue, where the light source and/or detector are not in contact with the tissue, such as in the case of camera-based measurements. The PPG data may be obtained at one or more wavelengths, such as 1, 2, 3, 4, 5, 6, 7, 8, 9, 10 or more wavelengths. In some examples, the incoming light is ambient light, such as sunlight. In an embodiment, PPG data may be obtained using a pulse oximeter which monitors the perfusion of blood, such as monitors the perfusion of blood to the dermis and subcutaneous tissue of the skin, and/or monitors the perfusion of blood through mucosal tissue. Apparatus and techniques for obtaining PPG data, such as pulse oximetry data, are well known in the art.

The second sensor 104 for independently measuring characteristics of the delivered compressions is optional. If used, it measures at least the compression rate, but it may also include compression acceleration, speed, depth, force, and pressure.

In the physiological signal, the dominant frequency components are (1) the fundamental chest compression frequency if chest compressions are being delivered, and (2) the fundamental spontaneous pulse rate if the heart beats again. The dominant frequency component is the fundamental chest compression rate if chest compressions are being delivered.

The analysis of the spectral components in the PPG/ECG and compression signals can be based on Fourier analysis, autoregressive modeling or wavelet analysis. To discriminate between the compression rate and the spontaneous pulse/heart rate, higher harmonics are analyzed as well, because the frequency difference between the higher harmonics is larger than the frequency difference between the fundamental components. Thus, by analyzing the harmonics the contrast between the spontaneous pulse/heart rate and the compression rate is improved. Furthermore, the harmonic series present in the PPG/ECG signal caused by compressions can be recognized by analyzing the harmonics in the series. Analysis of the harmonics can for instance comprise analyzing the number of harmonics and/or analyzing the total power in the harmonic series relative to the noise floor. In this way, the analysis of the harmonic series can obviate the need of an independent measurement of compressions.

The processing unit extracts the dominant components, i.e. fundamental frequency components of the physiological signal harmonic series, for subsequent display in the time-frequency representation. For clarity, only the fundamental chest compression rate and the fundamental spontaneous pulse rate are displayed on the screen, and higher harmonics of the chest compression rate and the spontaneous pulse rate are omitted. In the processing, however, the (energy of the) harmonics is taken into account to identify the dominant frequencies present in the signal.

Additionally, the processing unit may determine two quality indicators.

FIG. 3 shows a second example of display output including a first quality indicator 220 which shows the depth of the compressions derived from the compression measurement. It indicates whether the compression are within the range prescribed by the guidelines (5-6 cm), or whether the compressions are too shallow (<5 cm) or too deep (>6 cm). A second quality indicator 222 shows the strength of the spontaneous pulse component in the PPG signal based for example on the signal-to-noise ratio, or the number of harmonics in the PPG signal, or the accumulated energy of the harmonics in the harmonic series, or the stability of the pulse rate.

In another embodiment, the indicators can be incorporated in the time-frequency representation, via a color coding of the traces representing the fundamental compression rate and fundamental spontaneous pulse rate over time.

The indicators are of interest because during CPR, feedback on the quality of the CPR delivered and feedback on the condition of the patient are important. For example, delivering 100-120 compressions per minute is important to achieve high-quality CPR. The quality of CPR is associated with the CPR outcome. Also, studies have shown that real-time feedback devices improve the quality of CPR. Providing feedback on the rate at which chest compressions are delivered during CPR assists the caregiver in achieving the desired rate of 100-120 per minute.

The displayed information enables interruptions of chest compressions to be minimized to perform pulse checks. Furthermore, vasopressors may have detrimental effects on cardiovascular stability if administered just after the heart has started beating again. Showing the caregiver during ongoing compressions whether an underlying spontaneous pulse is present can prevent administration of vasopressors when these may have detrimental effects. Thus, administration of vasopressors can be guided so that when a spontaneous pulse is present, the clinician knows that vasopressors should not be administered.

Figure 4:
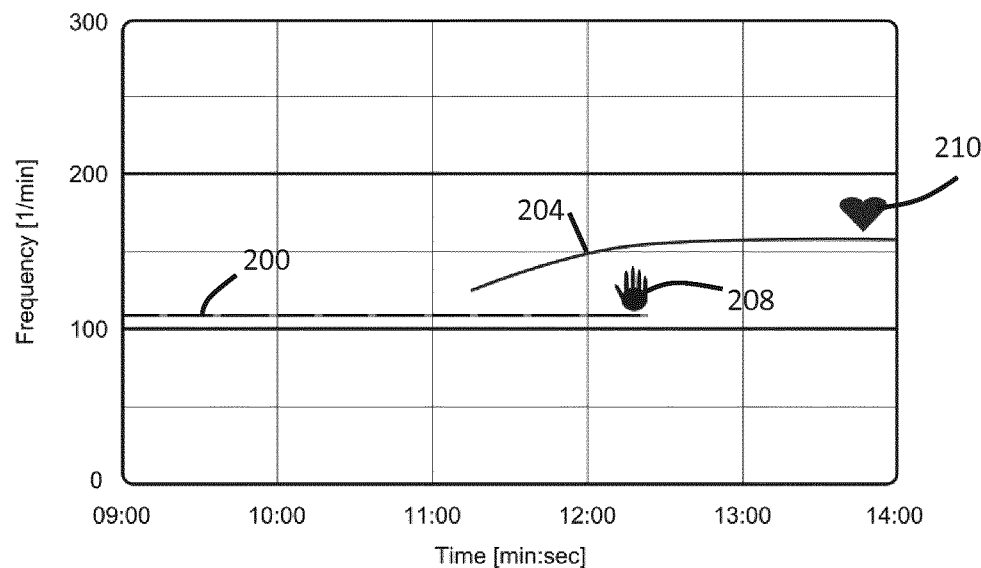
FIG. 4 shows a third example of possible display output.

FIG. 4 shows a third example of display output, in which the fundamental compression rate line 200 is segmented in order to mark the instants when compressions are shortly interrupted. During short interruptions, the rate at which compressions were delivered previously is maintained in the time-frequency representation for clarity. Only when the compression measurement indicates that compressions have been stopped for a longer period of time, the trace disappears from the time-frequency representation. To determine when the chest compressions have been interrupted, time-domain analysis is needed complementary to the frequency analysis to determine the chest compression rate.

For example, short interruptions in the chest compressions may be shown in a lighter color of the trace. When compressions are shortly interrupted, e.g., when the compression sensor detects no compressions for a period longer than 1 second but less than 5 seconds, the rate at which chest compressions were delivered previously is kept in the time-frequency representation but marked by the lighter color. Only when compressions are interrupted for a longer period of time, e.g., when the compression sensor detects no compressions for a period longer than 5 seconds, the compression trace is removed from the time-frequency representation. This approach is of particular interest for following the chest compression-rate during 30:2 CPR, when compressions are interrupted every thirty compressions to deliver two ventilations (so that an interruption of 3-5 seconds is expected).

Figure 5:
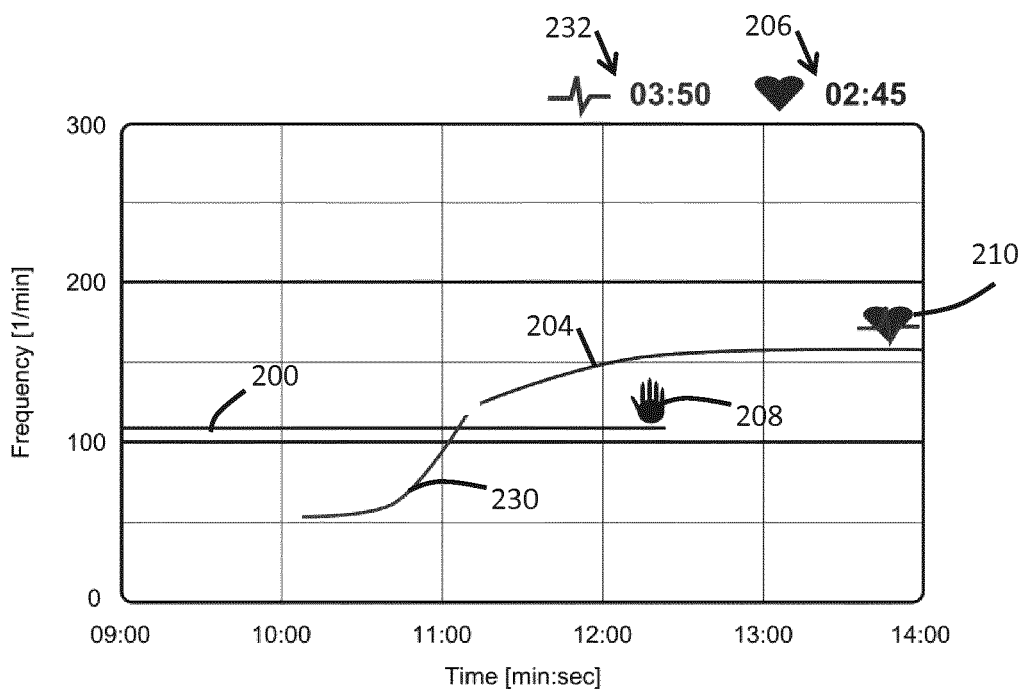
FIG. 5 shows a fourth example of possible display output.

The PPG signal can be replaced by an ECG signal in the examples above. Alternatively, the ECG and PPG signals can be combined in a single embodiment, to support detection of Pulseless Electrical Activity (PEA). A display output for this mode is illustrated in FIG. 5.

The fundamental compression rate is again shown as plot 200 and the fundamental spontaneous pulse rate is shown as plot 204. The fundamental heart rate is shown as plot 230 (which may be a different color to plot 204 for ease of recognition. The width of each plot may again indicate the variability of the frequency, i.e., the wider the line, the more variable the frequency is. The timer 206 again shows the time that a spontaneous pulse rate has been detected uninterruptedly. The new timer 232 shows the duration of the period that a heart rate has been detected uninterruptedly.

The fundamental heart rate is derived from an ECG signal.

The ECG signal shows that electrical activity of the heart resumes at about 10:10. At that point, a heart rate has been detected in the ECG signal, which is shown by the plot 230. A spontaneous pulse is detected in the PPG signal at about 11:15, at which point the plot 204 appears in the time-frequency representation.

In FIG. 5 a heart rate has been detected for 03:50 (from the start of plot 230) and a spontaneous pulse has rate has been detected for 02:45. (from the start of plot 204). If the heart rate disappears again, both timers will freeze. If the spontaneous pulse rate disappears, the corresponding timer will freeze. If the heart rate or spontaneous pulse rate re-appears, the corresponding timer will start running again from 00:00. Showing the duration that a heart rate and a spontaneous pulse rate have been detected uninterruptedly is meant to support the clinician in deciding when to interrupt the chest compressions to determine whether the spontaneous pulse is palpable and there is ROSC.

The time-frequency representation in FIG. 5 shows how the combination of ECG and PPG can support detection of pulseless electrical activity (PEA). Initially, between 10:10 and 11:15, the electrical activity of the heart does not lead to actual contractions, which clearly follows from the presence of a detected heart rate (plot 230) and absence of a detected pulse rate (plot 204). During this interval of PEA, the monitor clearly shows that CPR should be continued, as there is no perfusing pulse.

The term "Return of Spontaneous Circulation" (ROSC) as used in this application is understood as is known in the art, and refers to Clinical significance of return of pulse.

A patient can only have Return of Spontaneous Circulation (ROSC) when a perfusing and life-sustaining rhythm has been re-established, i.e., when the heart contracts again at a stable rate, resulting in cardiac output which is adequate in providing sufficient nutrients and oxygen to the tissues to keep the person alive. Therefore, by detecting the pulse rate, one may provide the clinician with information about the rate at which the heart contracts and pumps blood.

If this rate is too low, e.g., when the rate is below 1 Hz, the clinician can decide that there is no ROSC yet and that delivering chest compressions should be continued. Furthermore, when the detected pulse rate varies too much over time, this may indicate that the heart is not yet pumping in a stable fashion. This information can also be of use to the clinician to help him decide how to continue the CPR process.

When the heart is pumping again at a stable rate higher than, e.g., 1 Hz, the clinician can decide to further examine whether there is ROSC, by doing additional measurements (e.g., blood pressure, or end-tidal CO2). Presence of a stable pulse rate which is sufficiently high therefore is a prerequisite of ROSC: without such a rhythm, there will be no ROSC, and it will be of no use to do a further assessment of ROSC. On the other hand, presence of a stable, sufficiently high pulse rate in a PPG signal does not directly indicate that there is ROSC, because it does not provide the clinician with the information about the underlying blood pressure and/or level of perfusion. Additional measurements are required to determine this. Nonetheless, via embodiments of the present invention one can easily, and non-invasively obtain information about presence or absence of a stable, perfusing rhythm at a sufficiently high rate. Therefore, via the PPG-based pulse rate measurement, such as via embodiments of the present invention, the clinician can decide whether or not to stop chest compressions and do a further assessment of ROSC.

The example of FIG. 5 shows the benefit of combining information from multiple sensor types in order to derive additional information or to enable more reliable or simpler interpretation of data.

Another approach in accordance with the invention is to combine a photoplethysmography (PPG) signal and a capnography (CO2) signal (in particular an end-tidal CO2, ETCO2) to provide an indicator of cardiogenic output, which can support the clinician in detecting ROSC. In some examples, an electrocardiography (ECG) signal and a compression reference/motion signal are included as well.

By combining PPG and ETCO2, the interpretation of ETCO2 is made more specific. If ETCO2 increases without presence of a spontaneous pulse as detected from the PPG signal, it can be concluded that the increase in ETCO2 is not caused by spontaneous cardiac contractions. On the other hand, if the PPG signal shows presence of a spontaneous pulse, the ETCO2 signal can indicate the adequacy of the perfusion resulting from spontaneous cardiac contractions. Furthermore, the PPG signal provides the spontaneous pulse rate as explained above, which cannot be obtained from the ETCO2 signal, and PPG can show presence of a spontaneous pulse earlier than ETCO2. By combining PPG and ETCO2 a more reliable indicator of cardiogenic output is obtained compared to using either of the signals separately.

The additional information derived from the ETCO2 signal can thus be displayed to further guide the clinician during CPR. Although PPG can be used to detect the onset of pulses, it does not provide a measure of perfusion. Furthermore, PPG can detect presence of spontaneous pulses at sub-life-supporting blood pressures.

Currently, CPR guidelines state that capnography can be used to obtain an indication of return of spontaneous circulation (ROSC). The guidelines state that an end-tidal CO2 (ETCO2) level exceeding 40 mmHg can be considered indicative of ROSC. However, the disadvantages of ETCO2 alone are:

the response in ETCO2 when the heart resumes output may be relatively slow, taking approximately 0.5-2 min before reaching an ETCO2 level of about 30-40 mmHg.

interpretation of the actual level can be complicated and there is no clear cutoff between ROSC and no ROSC.

CO2 does not provide information on the spontaneous pulse rate.

By combining a PPG signal with an ETCO2 signal a stronger indication of a potential return of spontaneous circulation (ROSC) is provided. ROSC means a resumption of sustained and life-sustaining perfusing cardiac activity associated with significant respiratory effort after cardiac arrest. Here, a sudden and sustained increase in ETCO2 is interpreted as an indicator of perfusion, when the PPG signal shows presence of a spontaneous pulse. Furthermore, the interpretation of the ETCO2 level is more specific by the combination with a spontaneous pulse in the PPG signal.

If the PPG signal does not indicate a spontaneous pulse, a high ETCO2 level may be caused by for example hypoventilation. By taking into account ETCO2, a measure of circulation can be obtained which is useful to assess whether the level of circulation can be life-sustaining, which in turn can support the detection of ROSC.

Figure 6:
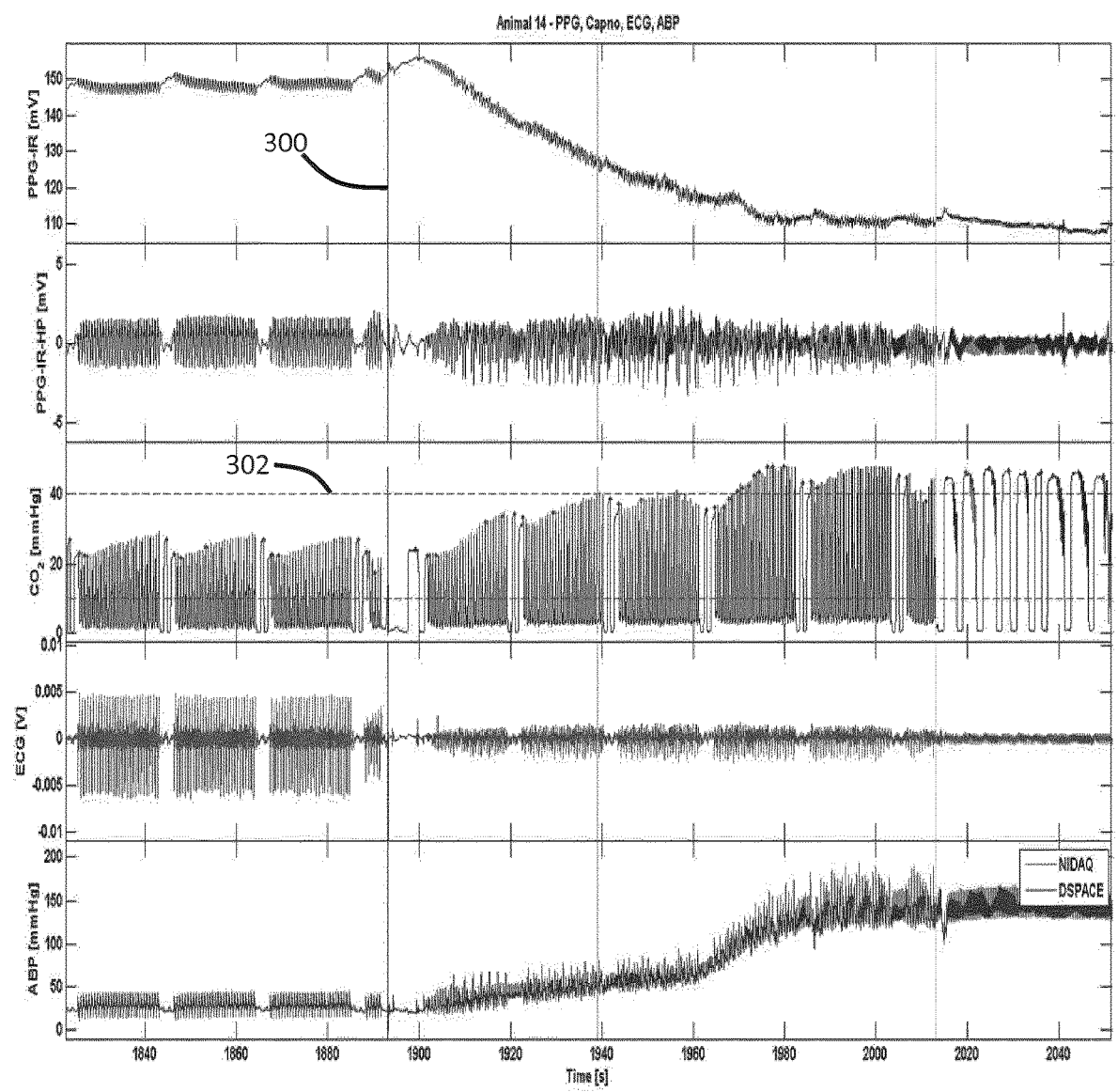
FIG. 6 shows further display output traces that may be provided and shows traces for an animal patient.
Figure 7:
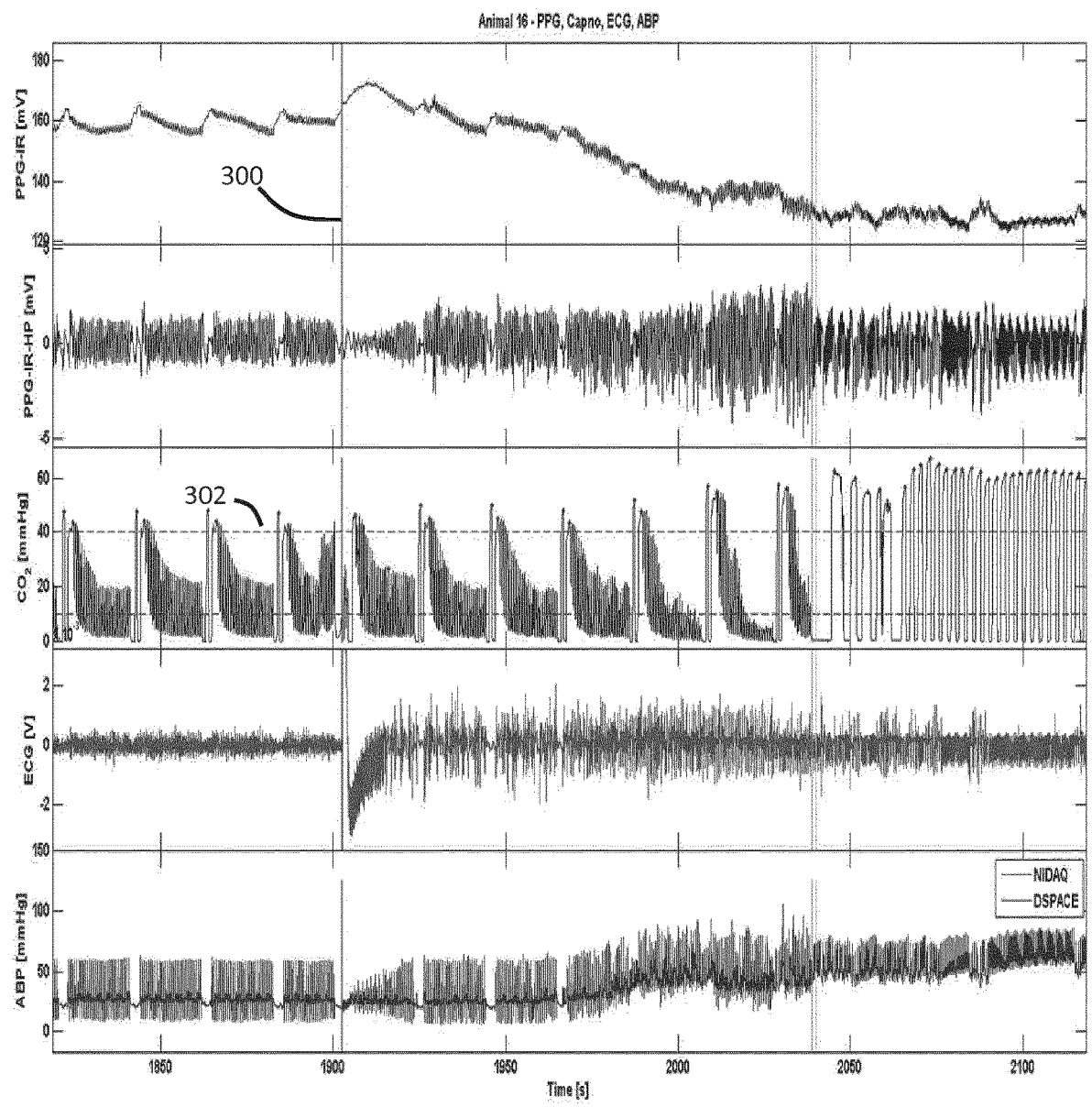
FIG. 7 shows the display output traces of FIG. 6 for another CPR (animal) patient.
Figure 8:
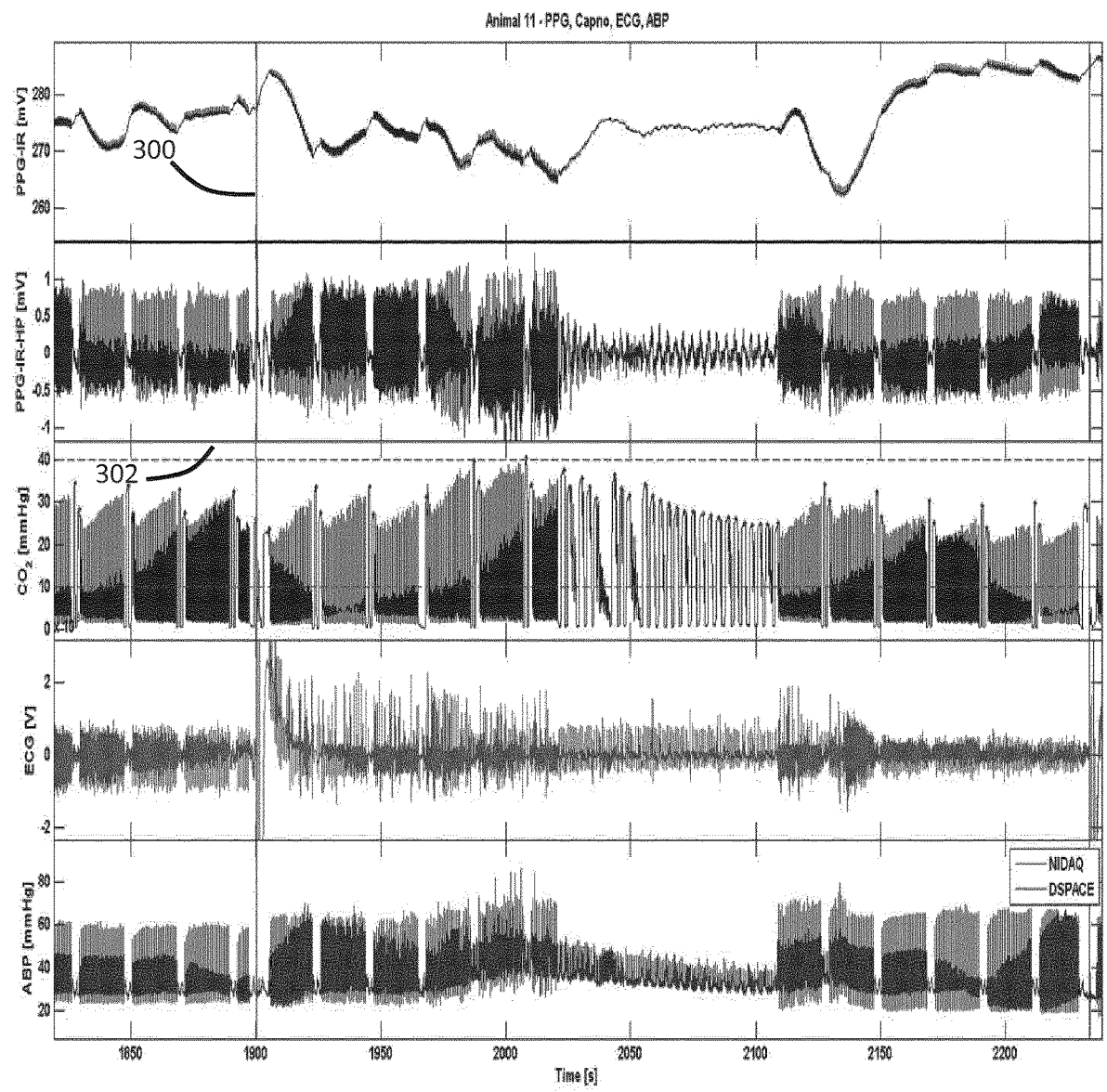
FIG. 8 shows the display output traces of FIG. 6 for yet another CPR (animal) patient.

The advantage of combining PPG and ETCO2 is described by FIGS. 6 to 8. They show measurement results obtained from pigs undergoing automated CPR with a protocol of thirty compressions alternated by two ventilations.

In all three figures, they show from top to bottom:
the measured infrared raw PPG signal;
the high-pass filtered infrared PPG signal;
the capnography signal;
the electrocardiography (ECG) signal; and
the arterial blood pressure (ABP) in the aortic arch.

Before the defibrillation shock (vertical line 300), the animal is in cardiac arrest. Cardiac arrest is confirmed by the PPG signal in this interval, as it shows a stable oscillating compression signal during the thirty compressions and no oscillations during the pauses for ventilations.

After the defibrillation shock, the PPG signal shows presence of an underlying spontaneous pulse via an increased complexity of the high-pass filtered PPG signal during compressions. Return of a spontaneous pulse is also shown by a decrease in the baseline of the PPG signal. After the defibrillation shock, spontaneous pulses can be observed in the PPG signal during the pauses for ventilations. Presence of a spontaneous pulse is confirmed by the increase in arterial blood pressure (ABP). The ETCO2 level considered in the examples is the one at the end of the first ventilation following a sequence of thirty compressions. The relationship between ETCO2 and ABP depends on how well the ventilations are controlled.

FIG. 6 shows an example in which the PPG signal shows presence of a spontaneous pulse earlier than ETCO2, i.e. before the ETCO2 level exceeds the 40 mmHg threshold 302 indicative of ROSC according to the CPR guidelines.

FIG. 7 shows an example in which the PPG signal makes the interpretation of the ETCO2 signal more specific. Already during the cardiac arrest phase before the line 300, the ETCO2 exceeds the 40 mmHg threshold 302 indicative of ROSC according to the CPR guidelines. In this interval, however, the PPG signal confirms cardiac arrest. Thus, the PPG signal makes the interpretation of the ETCO2 signal more specific. The PPG signal would prevent stopping CPR too early, by showing that a spontaneous pulse is actually absent. After the defibrillation shock, the PPG signal shows presence of a spontaneous pulse by an increased complexity and a decrease in the baseline of the PPG signal. Here a sustained rise in ETCO2 only occurs about 90 s after the defibrillation shock, which can be interpreted as an improvement in the perfusion.

FIG. 8 shows an example in which the ETCO2 signal can indicate the adequacy of the perfusion by cardiac contractions. The ETCO2 level does not ever exceed the 40 mmHg threshold considered indicative of ROSC according to the CPR guidelines. In this example, at about 2020 s, compressions were stopped as ROSC was considered to be achieved. However, the animal collapsed again and CPR had to be reinitiated at about 2110 s. In this interval, ETCO2 did not exceed the 40 mmHg threshold indicative of ROSC according to the CPR guidelines. So here the PPG signal would show that the heart has restarted beating which could withhold vasopressor administration, but the ETCO2 could prevent compressions from being stopped too early.

Thus, combining PPG and ETCO2 has the advantage of maintaining the early detection capability of PPG, while obtaining information about perfusion via ETCO2. Presence of a spontaneous pulse can be detected early via PPG, which can prevent administration of vasopressors, which can be detrimental when the heart just resumes cardiogenic output. The ETCO2 level can provide a measure of perfusion and thereby show whether the spontaneous circulation can be considered sufficient. When the spontaneous circulation is insufficient according to ETCO2, compressions should be continued on a beating heart.

The display outputs shown above in FIGS. 2 to 5 can be supplemented with a capnography signal trace. Additional support for the detection of ROSC is thus enabled by the ETCO2 level, which can provide an indication of the level of perfusion.

Figure 9:
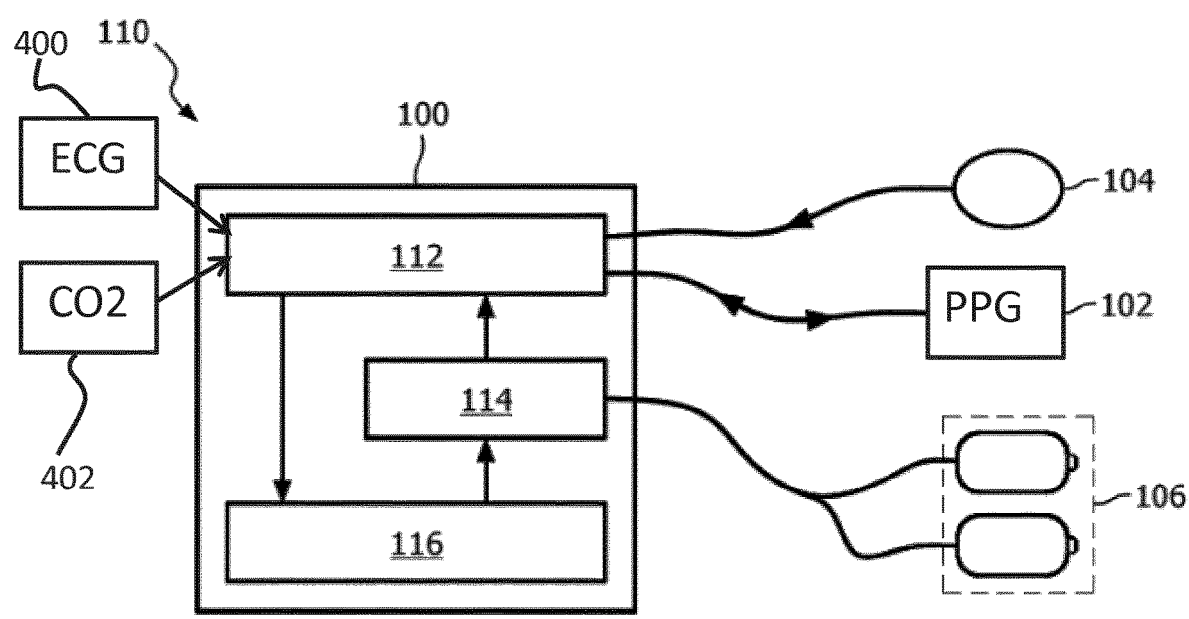
FIG. 9 shows a second example of a patient monitoring system in accordance with the invention.

FIG. 9 shows the system of FIG. 1 enhanced so that the processor receives inputs from an ECG sensor 400, a CO2 sensor 402 as well as the PPG sensor 102.

The displayed information then includes the fundamental frequency components of the PPG and compression signals, as explained above (as a frequency vs. time plot), but also a set of amplitude vs. time plots, including the ECG and CO2 signals. The raw PPG signal (which includes the baseline), and high pass filtered PPG signals as shown in FIGS. 6 to 8 may also be displayed. Another PPG based signal which may be represented is the high pass filtered PPG signal from which the compressions have been removed by further filtering.

Thus signals to present may include:
an electrocardiography (ECG) signal;
one or more photoplethysmography (PPG) based signals (i.e. with different possible filtering rules, and/or display of fundamental frequency components only on a frequency axis);
a capnography signal (end-tidal CO2, ETCO2);
a motion/compression reference signal.

The electrocardiography (ECG) signal may for instance be obtained via the defibrillation pads as mentioned above. The capnography signal can be obtained either via a mainstream or a side-stream measurement, from an intubated patient. Non-invasive alternatives also exist for measuring ETCO2. Algorithms exist for determining ETCO2 from capnography signals.

In addition to displaying various information as explained above, to enable a clinician to make an assessment, the system may process all of the received inputs to generate a single easy to interpret indication of cardiogenic output.

For example, the PPG and CO2 signals may be interpreted automatically to generate the following four indications, and they may be color coded on the display:

No Spontaneous Pulse

In this state, no spontaneous pulse is detected in the PPG signal. Detection of presence of a spontaneous pulse can for instance be done by identifying the spectral peak corresponding to the spontaneous pulse rate. If no spontaneous pulse rate is detected in the PPG spectrum, ETCO2 is not considered further.

Inadequate Spontaneous Pulse

In this state, a spontaneous pulse has been detected in the PPG signal, e.g., by identifying the spectral peak corresponding to the spontaneous pulse rate, but the spontaneous pulse rate is considered to be too low, e.g., below 60/min, to be able to generate a life-sustaining cardiac output in these conditions, or the beat-to-beat variation in the spontaneous pulse rate is considered to vary too much over time to be considered stable cardiac activity.

In this state, ETCO2 is not considered further.

Stable Spontaneous Pulse with Insufficient Circulation

In this state, a sufficiently high spontaneous pulse rate, e.g., above 60/min, has been detected of which the beat-to-beat variation is sufficiently small, indicating stable cardiac contractions. However, no sustained increase in ETCO2 has been detected, which exceeds a level of, e.g., 40 mmHg, which is considered to indicate insufficient circulation.

Potential ROSC

In this state, a sufficiently high spontaneous pulse rate, e.g., above 60/min, has been detected of which the beat-to-beat variation is sufficiently small, indicating stable cardiac contractions. In addition, a sustained increase in ETCO2 has been detected, which exceeds a level of, e.g., 40 mmHg, which is considered to indicate sufficient circulation.

When the "Potential ROSC" state is indicated, the clinician can consider interrupting the chest compressions, to further assess the potential ROSC. In case of an application for lay responders, the algorithm could prompt for checking the status of the patient in case of the "Potential ROSC" state.

The chest compression measurement (from sensor 104) may also be used. As explained above, this helps to discriminate better between compression-induced components and spontaneous pulse components in the PPG signal. It also assists in discriminating between compression-induced components and ventilation-related components in the capnography signal to robustly detect the ETCO2 signal. The motion/compression reference signals can be used as a basis for filtering to remove components from the PPG and capnography signals.

By using chest compression information, the following five identifications may be derived.

No Spontaneous Pulse

In this state, no spontaneous pulse is detected in the PPG signal. Detection of presence of a spontaneous pulse can for instance be done by identifying the spectral peak corresponding to the spontaneous pulse rate. Furthermore, the ETCO2 signal has not shown any sustained increase and is below a threshold of, e.g., 40 mmHg.

Spontaneous Pulse Rate≈Compression Rate?

In this state, no spontaneous pulse has been detected in the PPG signal during ongoing chest compressions, but a sustained increase has been detected in the ETCO2 level, such that it exceeded a threshold of, e.g., 40 mmHg. This could be indicative of ROSC, with a pulse rate about equal to the compression rate, which explains why no pulse rate was detected by spectral analysis of the PPG signal. In this situation the clinician could consider to shortly interrupt the chest compressions for, e.g., 5 s, to determine whether a spontaneous pulse can be observed in the PPG signal time trace when compressions are stopped.

Inadequate Spontaneous Pulse

In this state, a spontaneous pulse has been detected in the PPG signal, e.g., by identifying the spectral peak corresponding to the spontaneous pulse rate, but the spontaneous pulse rate is considered to be too low, e.g., below 60/min, to be able to generate a life-sustaining cardiac output in these conditions, or the beat-to-beat variation in the spontaneous pulse rate is considered to vary too much over time to consider the cardiac activity to be stable. At the same time, no sustained increase has been detected in ETCO2.

Stable Spontaneous Pulse with Insufficient Circulation

In this state, a sufficiently high spontaneous pulse rate, e.g., above 60/min, has been detected of which the beat-to-beat variation is sufficiently small, indicating stable cardiac contractions but no sustained increase in ETCO2 has been detected, which exceeds a level of, e.g., 40 mmHg, which is considered to indicate insufficient circulation.

Potential ROSC

In this state, a sufficiently high spontaneous pulse rate has been detected, e.g., above 60/min, of which the beat-to-beat variation is sufficiently small, indicating a stable cardiac contractions and a sustained increase in ETCO2 has been detected, which exceeds a level of, e.g., 40 mmHg, which is considered to indicate sufficient circulation.

As explained above, the PPG and capnography signals are analyzed during ongoing compressions. By making use of a reference signal for the chest compressions, obtained by, e.g., accelerometry, impedance, compression force, or radar, the algorithm can distinguish between compression components and spontaneous pulse components in the PPG signal and between compression components and ventilation components in the capnography signal.

Even more levels of indication may be provided by making use of an ECG signal as well as the PPG signal, capnography signal and a motion/compression reference signal. In this case, there may be seven different indications:

Cardiac Arrest

In this state, no heart rate is detected in the ECG signal, no spontaneous pulse is detected in the PPG signal, and no sustained increase in ETCO2 exceeding a threshold of, e.g., 40 mmHg has been detected. Detection of heart rate or presence of a spontaneous pulse can for instance be done by identifying the spectral peak corresponding to the heart rate and spontaneous pulse rate, respectively.

Heart Rate≈Spontaneous Pulse Rate≈Compression Rate

In this state, no heart rate and no spontaneous pulse rate have been detected in the ECG and PPG signals during ongoing chest compressions, but a sustained increase has been detected in the ETCO2 level, such that it exceeded a threshold of, e.g., 40 mmHg. This could be indicative of ROSC, with a heart rate and pulse rate about equal to the compression rate, which explains why no heart rate and pulse rate were detected by spectral analysis of the ECG and PPG signals. As explained above, in this situation the clinician could consider to shortly interrupt the chest compressions for, e.g., 5 s, to determine whether the ECG signal is organized and spontaneous pulses can be observed in the PPG signal time trace when compressions are stopped, and furthermore whether each R peak in the ECG signal leads to a pulse in the PPG signal.

Pulseless Electrical Activity

In this state, a heart rate has been measured in the ECG signal, but no pulse has been detected in the PPG signal, and no sustained increase in ETCO2 has been detected.

Inconsistent Spontaneous Pulse

A heart rate has been detected in the ECG signal, a pulse rate has been detected in the PPG signal, but no sustained increase in ETCO2 has been detected, and the pulse rate is below the heart rate, i.e., not every R-peak in the ECG signals leads to an actual cardiac contraction.

Consistent but Inadequate Spontaneous Pulse

A heart rate has been detected, a pulse rate has been detected, and they are equal but the spontaneous pulse rate is considered to be too low, e.g., below 60/min, to be able to generate a life-sustaining cardiac output in these conditions, or the beat-to-beat variation in the spontaneous pulse rate is considered to vary too much over time to consider the cardiac activity stable. At the same time, no sustained increase has been detected in ETCO2.

Stable Spontaneous Pulse with Insufficient Circulation

In this case a heart rate and a pulse rate have been detected, and they are equal. A sufficiently high spontaneous pulse rate, e.g., above 60/min, has been detected of which the beat-to-beat variation is sufficiently small, indicating stable cardiac contractions. However, no sustained increase in ETCO2 has been detected, which exceeds a level of, e.g., 40 mmHg, which is considered to indicate insufficient circulation.

Potential ROSC

In this state, a heart rate and a pulse rate have been detected, and they are equal. There is a sufficiently high spontaneous pulse rate detected, e.g., above 60/min, of which the beat-to-beat variation is sufficiently small, indicating stable cardiac contractions. Furthermore a sustained increase in ETCO2 has been detected, which exceeds a level of, e.g., 40 mmHg, which is considered to indicate sufficient circulation.

As explained above, when the "Potential ROSC" state is indicated, the clinician can consider interrupting the chest compressions, to further assess the potential ROSC.

Displaying frequency vs. time plots as described above enables easy determination of the pulse rate as well as visual separation of the chest compression components and the pulse rate components. Displaying the amplitude vs. time waveforms enables beat-to-beat or compression-to-compression assessment of the signals by the clinician and allows for the early detection of presence of a spontaneous pulse in the PPG signal by a decrease in the PPG baseline, and/or an increased complexity of high pass filtered PPG signal and/or appearance of a spontaneous pulse in a PPG signal with the chest compression component filtered out.

A simple indicator which outputs one of the indications as explained above supports the clinician in interpreting the waveforms.

Instead of or as well as a time history of the compression frequency and pulse frequency, the current values may be displayed numerically, as well as the current ETCO2 value, and an integral of the CO2 over one ventilation or a series of compressions.

It will be seen from the description above that there are two aspects to the invention, and they may be combined or used individually. The first aspect is the extraction of fundamental components of frequency series present in a physiological signal (e.g. PPG) to enable easy detection of ROSC. The second aspect is the combination of a capnography signal and a PPG signal to provide better ease of interpretation. Further additional signals may then be combined to provide additional levels of interpretation and analysis. The second aspect provides a device for supporting determination of return of spontaneous circulation, ROSC, during an associated cardiopulmonary resuscitation, CPR, procedure which is being performed on an associated patient, the device comprising:

a first input for receiving a first signal from a PPG sensor;
a second input for receiving a second signal from a CO2 sensor;
a processor, which is adapted to:
perform analysis of the first and second signals to provide an evaluation of whether or not there has been has been a potential ROSC and provide an output which provides the evaluation and advised action to a user.

The output may be a displayed indicator. In addition, amplitude vs. time traces may be provided of the PPG signal and the CO2 signal, as well as signals derived from the PPG signal by filtering, such as a signal with the PPG baseline removed, the signal with a baseline and a signal with components resulting from CPR compressions filtered out.

The invention is of interest for advanced cardiopulmonary resuscitation (CPR) such for in-hospital CPR as part of a monitor-defibrillator, or for out-of-hospital CPR by medical professionals. It may be used in advanced AEDs.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

The invention claimed is:

1. A device for supporting determination of return of spontaneous circulation, ROSC, during an associated cardiopulmonary resuscitation, CPR, procedure which is being performed on an associated patient, the device comprising:
an input for receiving a signal from a sensor for sensing a physiological signal of the patient;
a processor, which is adapted to:
perform frequency analysis of the physiological signal;
detect and discriminate compression-induced components and spontaneous pulse components within the physiological signal, wherein the spontaneous pulse component includes a stable fundamental spontaneous pulse component and one or more arrhythmic spontaneous pulse components; and
provide an output based on the detected compression-induced and spontaneous pulse components within the physiological signal to support determination that there has been ROSC; and
a display device,
wherein the processor is adapted to control the display device to output an image which shows the compression-induced components and spontaneous pulse components within the physiological signal over time as a frequency-time plot, and further wherein the stable fundamental spontaneous pulse component and the arrhythmic spontaneous pulse components are displayed when spontaneous circulation returns to the associated patient.

2. A device as claimed in claim 1, wherein the processor is further adapted to extract dominant fundamental frequency components of harmonic frequency series within the physiological signal, and to control the display device to output the image based on the extracted dominant fundamental frequency components.

3. A device as claimed in claim 2, wherein the processor is adapted to perform frequency analysis of at least the dominant fundamental frequency components and first harmonic components present in the physiological signal.

4. A device as claimed in claim 3, wherein the processor is adapted to perform frequency analysis of at least second harmonic components present in the physiological signal.

5. A device as claimed in claim 1, wherein the sensor comprises an ECG sensor or a PPG sensor.

6. A device as claimed in claim 5, further comprising a further sensor or sensors for sensing:
one or more CPR compressions; and/or
a capnography signal.

7. A device as claimed in claim 1, wherein the processor is adapted to determine the quality of any determined potential ROSC.

8. A device as claimed in claim 1, wherein the processor is adapted to control the display device to output the image which shows:
the quality of one or more CPR compressions; and/or
the quality of any determined potential ROSC.

9. A method for supporting determination of return of spontaneous circulation, ROSC, during an associated cardiopulmonary resuscitation, CPR, procedure which is being performed on an associated patient, the method comprising:
sensing a physiological signal of the patient;
performing frequency analysis of the physiological signal;
detecting and discriminating compression-induced components and spontaneous pulse components within the physiological signal, wherein the spontaneous pulse component includes a stable fundamental spontaneous pulse component and one or more arrhythmic spontaneous pulse components; and
providing an output on a display device based on the detected compression-induced and spontaneous pulse components within the physiological signal to support determination that there has been ROSC, wherein the output shows the compression-induced components and spontaneous pulse components within the physiological signal over time as a frequency-time plot, and further wherein the stable fundamental spontaneous pulse component and the arrhythmic spontaneous pulse components are displayed when spontaneous circulation returns to the associated patient.

10. A method as claimed in claim 9, comprising extracting dominant fundamental frequency components of harmonic frequency series within the physiological signal, and providing an output based on the extracted dominant fundamental frequency components.

11. A method as claimed in claim 10, comprising performing frequency analysis of at least the dominant fundamental frequency components and first harmonic components present in the physiological signal, and optionally also at least second harmonic components present in the physiological signal.

12. A method as claimed in claim 9, wherein the physiological signal comprises an ECG signal or a PPG signal.

13. A method as claimed in claim 9, further comprising sensing one or more CPR compressions and determining the quality of the CPR compressions.

14. A method as claimed in claim 9, wherein the output shows:
   the quality of one or more CPR compressions; and/or
   the quality of any determined potential ROSC.

15. A non-transitory computer readable medium storing a computer program product for supporting determination of return of spontaneous circulation (ROSC) during an associated cardiopulmonary resuscitation (CPR) procedure which is being performed on an associated patient, comprising instructions configured to:
   sense a physiological signal of the patient;
   perform frequency analysis of the physiological signal;
   detect and discriminate compression-induced components and spontaneous pulse components within the physiological signal, wherein the spontaneous pulse component includes a stable fundamental spontaneous pulse component and one or more arrhythmic spontaneous pulse components; and
   provide an output on a display device based on the detected compression-induced and spontaneous pulse components within the physiological signal to support determination that there has been ROSC, wherein the output shows the compression-induced components and spontaneous pulse components within the physiological signal over time as a two-dimensional frequency-time plot, and further wherein the stable fundamental spontaneous pulse component and the arrhythmic spontaneous pulse components are displayed when spontaneous circulation returns to the associated patient.

* * * * *